(12) United States Patent
Bauer (10) Patent No.: US 11,504,474 B2
(45) Date of Patent: Nov. 22, 2022

(54) AUTO INJECTOR FOR OXYGEN REDUCED PACKAGING

(71) Applicant: Inject Pharma Sweden AB, Bromma (SE)

(72) Inventor: Sebastian Helmut Jose Bauer, Enskede (SE)

( * ) Notice: Subject to any disclaimer, the term of this patent is extended or adjusted under 35 U.S.C. 154(b) by 264 days.

(21) Appl. No.: 16/956,210

(22) PCT Filed: Dec. 21, 2018

(86) PCT No.: PCT/EP2018/086674
§ 371 (c)(1),
(2) Date: Jun. 19, 2020

(87) PCT Pub. No.: WO2019/122368
PCT Pub. Date: Jun. 27, 2019

(65) Prior Publication Data
US 2020/0390975 A1 Dec. 17, 2020

(30) Foreign Application Priority Data
Dec. 21, 2017 (SE) .................................. 1751621-2

(51) Int. Cl.
*A61M 5/20* (2006.01)
*A61L 2/20* (2006.01)
(Continued)

(52) U.S. Cl.
CPC .............. *A61M 5/20* (2013.01); *A61L 2/206* (2013.01); *A61M 5/002* (2013.01); *B65B 31/06* (2013.01);
(Continued)

(58) Field of Classification Search
CPC ................... A61M 5/20; A61M 5/002; A61M 2005/3123; A61M 2205/15;
(Continued)

(56) References Cited

U.S. PATENT DOCUMENTS

| 3,485,239 A | 12/1969 | Vanderbeck | |
|---|---|---|---|
| 2004/0182736 A1* | 9/2004 | Mesa | B32B 27/36 206/521 |
| 2010/0174268 A1* | 7/2010 | Wilmot | A61J 1/062 141/2 |

(Continued)

FOREIGN PATENT DOCUMENTS

| WO | 03039632 A2 | 5/2003 | |
|---|---|---|---|
| WO | WO-2013154954 A1 * | 10/2013 | A61M 5/20 |

OTHER PUBLICATIONS

Swedish Search Report from corresponding Swedish Application No. 1751621-2, dated May 30, 2018, 10 pages.

(Continued)

*Primary Examiner* — Lauren P Farrar
(74) *Attorney, Agent, or Firm* — Tucker Ellis LLP (57) ABSTRACT

The present invention relates to an auto injector (1) comprising a prefilled liquid medicament container, a hollow auto injector body (2) housing the medicament container. The auto injector body (2) has an elongated part, a first end side (21) and a second end side (22) and at least one through hole (3) arranged between the end sides (21, 22). The through holes (3) allow for flow of gas through the auto injector body (2) when the auto injector body (2) houses the medicament container. The invention further relates to a method comprising inserting the auto injector (1) into the package via an opening in a non-inert environment, and, in a non-inert environment and under atmospheric pressure: replacing the air in the package with inert atmosphere by one or several cycles of removing air and inserting inert gas through the opening, wherein the air and inert gas in part flows through the at least one through hole (3) of the auto injector (1). The method further comprises sealing the opening under vacuum.

13 Claims, 9 Drawing Sheets

(51) Int. Cl.
    *A61M 5/00*          (2006.01)
    *B65B 31/06*        (2006.01)
    *A61M 5/31*         (2006.01)

(52) U.S. Cl.
    CPC ..... *A61L 2202/182* (2013.01); *A61L 2202/24* (2013.01); *A61M 2005/3123* (2013.01); *A61M 2205/15* (2013.01); *A61M 2205/584* (2013.01)

(58) Field of Classification Search
    CPC .............. A61M 2205/584; A61L 2/206; A61L 2202/182; A61L 2202/24; B65B 31/06
    See application file for complete search history.

(56) References Cited

U.S. PATENT DOCUMENTS

| | | |
|---|---|---|
| 2013/0018324 A1 | 1/2013 | Reynolds et al. |
| 2014/0012229 A1 | 1/2014 | Bokelman et al. |
| 2014/0018742 A1* | 1/2014 | Sodhi .................... A61M 5/002 604/199 |
| 2014/0207106 A1* | 7/2014 | Bechmann .......... A61M 5/3204 604/506 |
| 2016/0279350 A1* | 9/2016 | Besirli ................. A61M 5/422 |
| 2017/0008686 A1* | 1/2017 | Tanoguchi ........... B65D 75/326 |
| 2017/0312433 A1 | 11/2017 | Edwards et al. |

OTHER PUBLICATIONS

International Search Report and Written Opinion from corresponding International Application No. PCT/EP2018/086674, dated Feb. 20, 2019, 11 pages.

\* cited by examiner

AUTO INJECTOR FOR OXYGEN REDUCED PACKAGING

TECHNICAL FIELD

The present invention relates to an auto injector for administrating a medical composition and a method for filling a package with the auto injector.

BACKGROUND

Auto injectors are intended to be used to self-administer drugs. There are many different kinds of designs of auto injectors, but the common denominator is that they are for overcoming the hesitation associated with self-administrating drugs. They are usually a needle-based device with a pre-loaded syringe. The needle is shielded before use so that it is not possible to hurt oneself on it.

When designing an auto injector, it is not only the functionality that needs to be considered. The usability is as important since an auto injector is often used by people untrained in using them. It needs to be very clear how to use it to a person picking up the device. For example, epinephrine auto injectors, for use by people who are at risk for anaphylaxis, are often used under time pressure when it is important that the patient receives the injection quickly after an allergen exposure. In such cases it is even more crucial that the auto injector is easy to use, and self-explanatory in its design.

Another issue with designing auto injectors is that the life span of the drug is affected by the design. For example, some drugs are very sensitive to oxygen, all drugs are sensitive to plunger movement at transportation, because sterility can be compromised, and some are sensitive to light. Oxidative degradation is a chemical process that renders many drugs inactive, by degrading the active ingredient, or makes the product unusable, by changing the properties of the excipients or by changing the physical properties, parts or all. Furthermore, oxidation can also have a negative impact on plastic components of the auto injector and thus reduce reliability and shelf life of the mechanical auto injector.

Auto injectors are often packaged in a protective packaging to protect them before use. For drugs that are sensitive to oxygen and/or other atmospheric gases, the process of packaging the auto injector is very important and often onerous.

There is a need for simplifying the process of packaging auto injectors and at the same time providing an auto injector that is easy to use.

SUMMARY

It is an aim of the present invention to at least partly overcome the above problems, and to provide an improved method and device for packaging of auto injectors.

The present disclosure aims to provide an improvement of the packaging of auto injectors by providing an auto injector which is possible to package in a non-inert environment. The disclosure also provides a package and a packaged auto injector set.

This aim is achieved by the device as defined in claims 1, 12 and 13 and the method defined in claim 14.

According to an embodiment of the disclosure, it comprises an auto injector for administrating a medical composition. The auto injector comprises a prefilled liquid medicament container comprising the medical composition, a hollow auto injector body defining a space housing the medicament container, wherein the auto injector body is elongated having an elongated part, a first end side and a second end side opposite the first end side and at least one through hole (3) arranged through the auto injector body between the first and second end sides, whereby the at least one through hole allow for flow of gas through the auto injector body when the auto injector body houses the medicament container. By designing an auto injector with through holes where gas can flow through it, it is possible to package it such that the air inside the auto injector is removed in a simple, fast and reliable manner. In the method for packaging described below, air may be removed from the package and inert gas may replace it. The through hole will help in emptying the package from air by allowing the air, and the protective gas that is to replace the air, to flow through the auto injector; otherwise there is a risk that there will form air pockets in the auto injector. In other words, the through holes make sure that there are no air pockets inside of the auto injector such that the amount of air removed from the package is maximized. The design thus allows for minimizing the presence of unwanted atmospheric gases in the package with the auto injector.

According to some aspects, the at least one through hole each comprises two through hole openings. In other words, each through hole has an opening in each end of the auto injector. It should be noted that if there are more than one through hole, they may share the same opening through the auto injector but have different openings in the end sides.

According to some aspects, the through hole openings have a diameter equal to or larger than 0.5 mm. The size of the through hole opening will determine the flow rate of gas through it. The hole should be large enough to allow for gas to flow fast enough to be useful when packaging the auto injector. The size needed for the through hole will depend on what gases are used, what kind of technique is used for removing the air and filling with inert gas, the number of through hole openings and the shape of the through hole; the shape may have a big influence on how the gas flows.

According to some aspects, at least one through hole opening is located partly on an end side and partly on the elongated part of the auto injector such that the opening is located on the edge of the end side. A through hole that goes over the edge of the end side and to the elongated part may prevent air pockets to form in the package on both the end sides and on the sides of the auto injector.

According to some aspects, the at least one through hole comprises at least two through holes with through hole openings symmetrically arranged on the first and second end sides. If several through holes are used, they may be arranged symmetrically on the end sides such that it is aesthetically pleasing. The symmetry may also be beneficial in preventing air pockets because it ensures a maximum coverage of the end sides with through holes.

According to some aspects, the medicament container is at least partly transparent and the auto injector body is provided with at least two apertures arranged on opposite sides of the medicament container allowing for visual control of the medical composition inside the container, wherein the apertures form a visual line through the auto injector body which is non parallel with the longitudinal axis of the auto injector body. Visual control of the medical composition, i.e. the drug inside the auto injector, is important so that the user can easily check if there is something wrong with the drug; for example, if the container is broken such that the drug is leaking out or that the drug has changed colour, for example due to oxygen exposure.

According to some aspects, the at least one through hole is connected with the at least two apertures inside the auto injector such that the gas can flow between the at least one through hole and the apertures. This aspect allows for gas to flow from one end to the other but also from the sides to the ends. This may further prevent air pockets from forming in the packaging process.

According to some aspects, the at least two apertures are arranged as a through hole through the auto injector body which is perpendicular to the at least one through hole arranged between the first end side and the second end side. This is an example of how the through holes are arranged with respect to each other.

According to some aspects, the at least one of the end sides comprises a recess and each through hole opening on that side is arranged at a wall of said recess so that each through hole opening is arranged perpendicular to the end side. The through hole openings, i.e. holes or slits, are positioned in such way that ventilating gas that enters through the holes can continue through the body of the auto injector and leave the auto injector on the opposite side of the auto injector. The through hole openings are designed in such way that the end user will not assume that the hole could be the place where the needle will emerge from the penetrating device. This is because the end user may be confused about which side is to be put against his/her body when using the auto injector if both sides have holes where it can be expected that a needle will come out upon usage. The through hole openings can therefore be designed such that they are less noticeable and that there is no direct line to the inside of the auto injector. By doing so, confusion of the end user with respect to the purpose of such openings can be minimized. Further, ingress of dirt/dust is more difficult.

According to some aspects, the medical composition comprises adrenaline. Adrenaline is sensitive to oxygen and it would be beneficial to use the auto injector according to the disclosure.

According to some aspects, the medical composition comprises a chemical oxygen scavenger. Chemical oxygen scavengers are used to prevent oxidative degeneration of the medical composition. It is used to further increase the shelf life of the auto injector.

According to some aspects, the chemical oxygen scavenger comprises sodium metabisulfite. Sodium metabisulfite is an effective chemical oxygen scavenger.

According to some aspects, the concentration of sodium metabisulfite in the medical compound is below or equal to 0.21 mg/ml. It is desirable to use as little sodium metabisulfite as possible since it can affect the medical composition.

According to an embodiment of the disclosure, it comprises a package for an auto injector according to any of the above, wherein the package is a pouch and the inside of the pouch is at least 70 mm longer than the length of the auto injector and has a maximum width, at the most narrow part of the pouch, of 30 mm wider than the width of the auto injector. An advantage with an auto injector which has through holes between the end sides is that the package can be made much more narrow than conventional packages. This is because air behind the auto injector will be evacuated through the through holes and not via the sides of the auto injector. This reduces the amount of packaging needed and it also makes the packaged auto injector easier to handle for the end user.

According to an embodiment of the disclosure, it comprises a packaged auto injector set comprising the package according to above filled with the auto injector according to any of the above, wherein the package filled with the auto injector is snugly arranged in a neoprene sleeve such that the movement of the auto injector relative the package is prevented. Since the package can be made narrow due to the through holes, there will not be a lot of packaging material around the auto injector. It is therefore easy to store this packaged auto injector set in a neoprene sleeve; there is not a lot of package that needs to be held in when putting it in the sleeve. The neoprene sleeve protects the packaged auto injector from physical damage, keeps the temperature of the auto injector more constant and minimizes movement of the packaged auto injector and thus minimizes friction which can lead to punctures.

According to an embodiment of the disclosure, it comprises a method for filling a package with an auto injector according to any one of the above aspects. The package comprises an opening. The method comprises inserting the auto injector into the package via the opening in a non-inert environment, and, in a non-inert environment and under atmospheric pressure: replacing the air in the package with inert atmosphere by one or several cycles of removing air and inserting inert gas through the opening, wherein the air and inert gas in part flows through the at least one through hole of the auto injector. The method further comprises sealing the opening under vacuum. As previously discussed, the through holes allow for the auto injector to be packaged in a non-inert environment according to above because they allow for oxygen to leave the package efficiently through the holes and fills the whole package, including the through holes inside the auto injector with inert gas. The achieved efficiency in removing air and inserting inert gas in the package and partly through the through holes makes it possible to perform these steps under atmospheric pressure. That is, the packaging does not need to be performed under vacuum, or only with slight negative pressure, avoiding and/or minimizing plunger movement, for syringes containing gas bubble, during pouching.

According to some aspects, the air is removed using a nozzle type vacuum sealing machine. Such a machine has a nozzle that is inserted in the opening of the package and removes the air through the nozzle. This type of machine provides a local point in the opening for removing the air which is an effective way of only removing the air that is in the package.

BRIEF DESCRIPTION OF THE DRAWINGS

The invention will now be explained more closely by the description of different embodiments of the invention and with reference to the appended figures.

DETAILED DESCRIPTION

Aspects of the present disclosure will be described more fully hereinafter with reference to the accompanying drawings. The device and method disclosed herein can, however, be realized in many different forms and should not be construed as being limited to the aspects set forth herein. Like numbers in the drawings refer to like elements throughout.

The terminology used herein is for the purpose of describing particular aspects of the disclosure only, and is not intended to limit the invention. As used herein, the singular forms "a", "an" and "the" are intended to include the plural forms as well, unless the context clearly indicates otherwise.

Unless otherwise defined, all terms used herein have the same meaning as commonly understood by one of ordinary skill in the art to which this disclosure belongs.

The term "adrenaline" is defined as adrenaline, also known as epinephrine, and salts thereof. Such salts include, but are not limited to, adrenaline tartrate and adrenaline hydrochloride.

Figure 1:
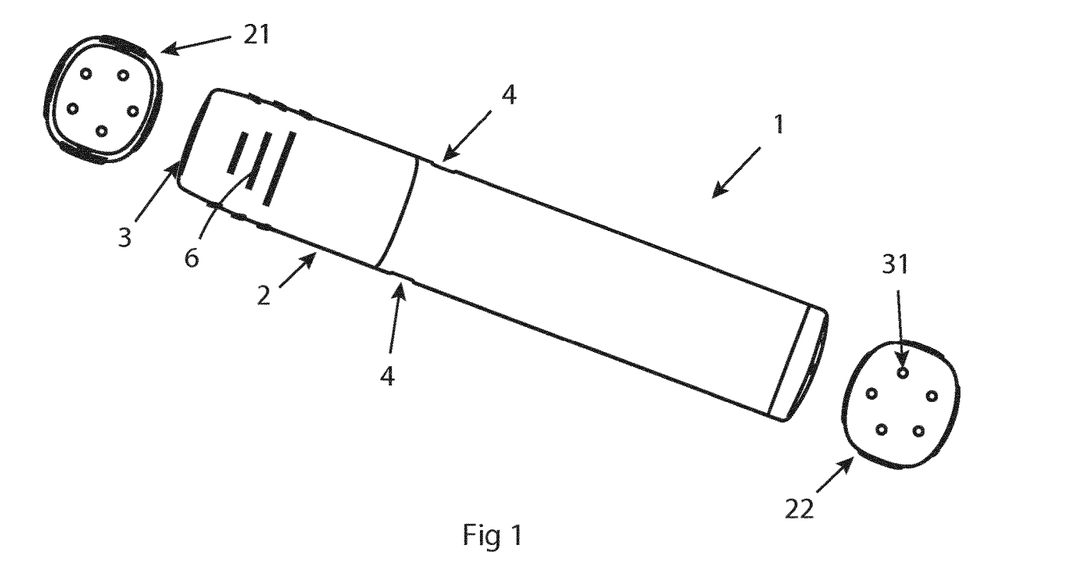
FIG. 1 shows an example of an auto injector with through holes and views of the ends

FIG. 1 shows an illustration of an auto injector 1 with through holes 3 and views of the ends. In this example there are five through hole openings in each end. There are also grips 6 on the sides of the auto injector for giving a good grip to the user when handling the auto injector. The grips are for example rubber ridges.

Figure 2:
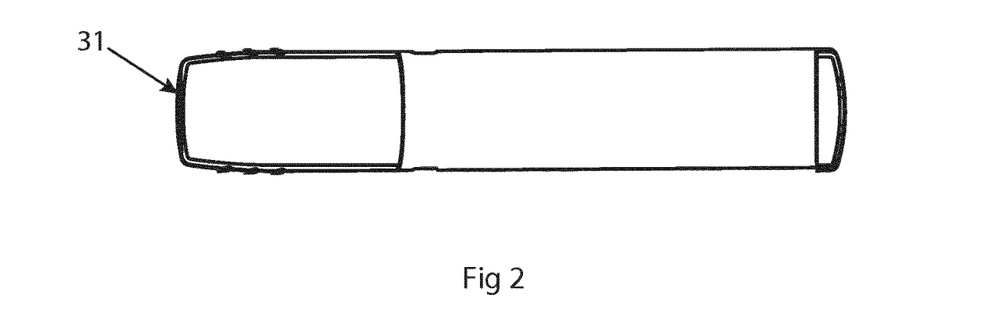
FIG. 2 shows an example of a cross section of an auto injector with through holes
Figure 3:
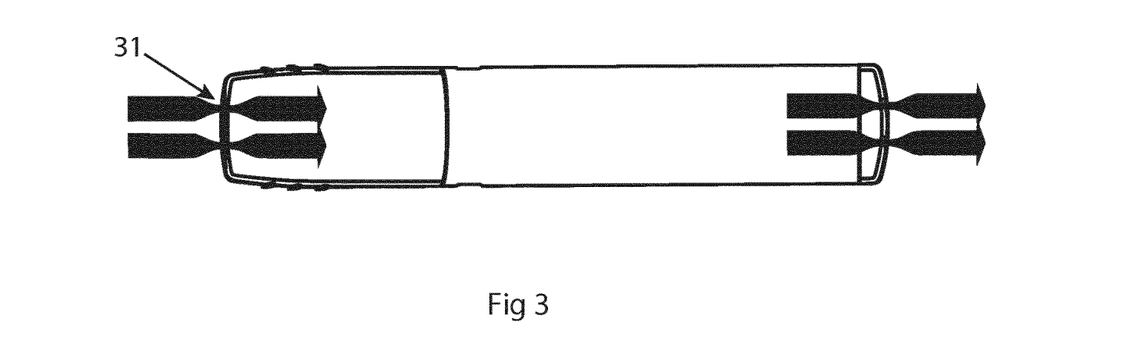
FIG. 3 shows an example of a cross section of an auto injector with through holes and gas flow indicated as arrows

FIGS. 2 and 3 shows an example of a cross section of an auto injector 1 with through holes 3 where FIG. 3 illustrates gas flowing in and out of the auto injector. The figures are examples of auto injectors according to some aspects of the disclosure. The through holes 3 may be varied in number and shape as will be described further below.

Figure 4:
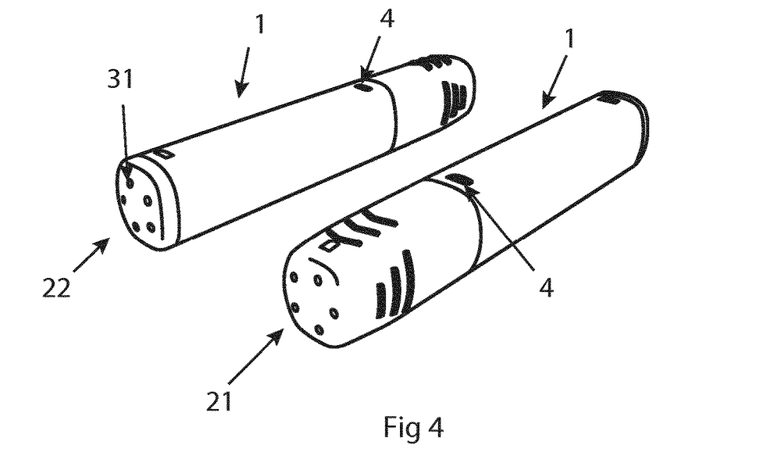
FIG. 4 shows an example of an auto injector with through holes from two view points
Figure 5:
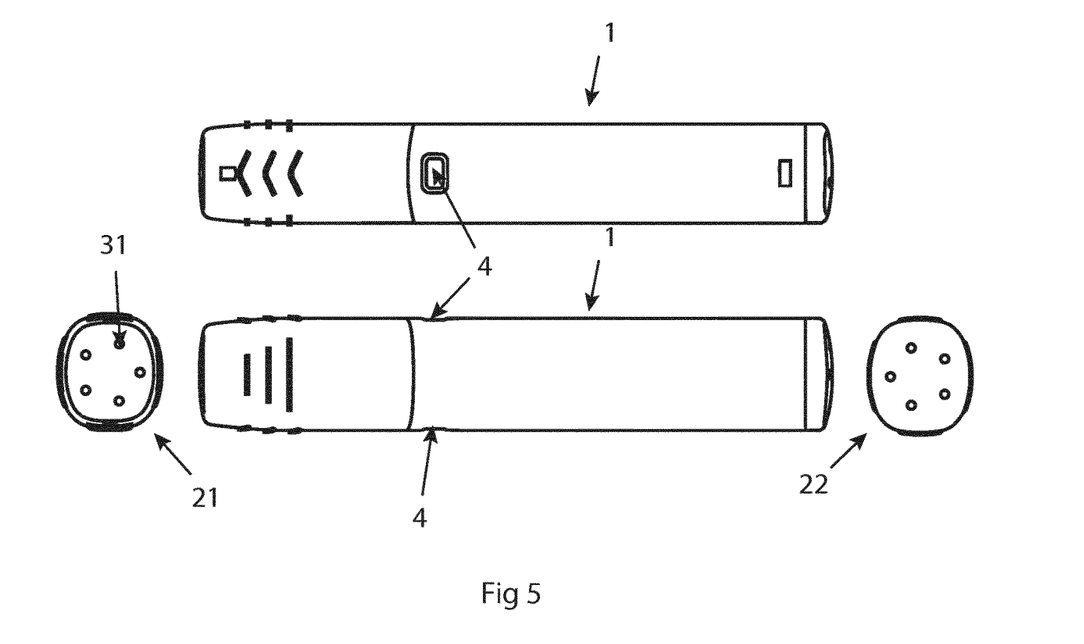
FIG. 5 shows an example of an auto injector from four viewpoints

FIGS. 4 and 5 are further views of example auto injectors. The illustrated auto injectors have 5 through holes with openings arranged in a symmetrical circular shape at the ends.

The auto injector 1 in this disclosure is an auto injector 1 for administrating a medical composition. The auto injector 1 comprises a prefilled liquid medicament container comprising the medical composition. Other common terms for the prefilled medicament container are primary packaging and primary containers. The prefilled medicament container is for example a syringe. The syringe may be spring loaded to push it out when injecting the drug. The prefilled medicament container is for example a prefilled syringe with a staked-on needle and having permeability to oxygen, e.g. a prefillable syringe with a staked-on needle and a rigid or flexible needle shield, which is sterilized by Eto (ethylene oxide) and thus permeable for oxygen. Oxygen permeable primary containers are very common, since sterilization is often performed by Eto gas which requires gas permeability of e.g. the needle shield. Other sterilization methods have other disadvantages. Radiation sterilization discolors glass, autoclavation does only allow for use of bulk syringes. There are many types of medicament containers that can be used in an auto injector 1 and for this disclosure, it is not relevant which one is used. The auto injector 1 may be any medical injection device comprising the features defined in claim 1. In other words, the content of the disclosure can be applied to any medical injection device, including auto injectors.

The primary container may be filled, aseptic or sterilized by terminal sterilization, with drug product either bubble free, if drug viscosity allows, or containing an inert gas bubble. The drug formulation can contain an oxygen scavenger, such as sodium metabisulfite, ascorbic acid etc., if residual oxygen, which is unavoidable during filling and packaging has to be scavenged. Thus, according to some aspects, the medical composition comprises a chemical oxygen scavenger. Chemical oxygen scavengers are used to prevent oxidative degradation of the medical composition. It is used to further increase the shelf life of the auto injector 1. According to some aspects, the chemical oxygen scavenger comprises sodium metabisulfite. Sodium metabisulfite is an effective chemical oxygen scavenger. According to some aspects, the concentration of sodium metabisulfite in the medical compound is below or equal to 0.21 mg/ml. Preferably, the concentration of sodium metabisulfite in the medical compound is below or equal to 0.15 mg/ml. More preferably, the concentration of sodium metabisulfite in the medical compound is below or equal to 0.1 mg/ml. Even more preferably, the concentration of sodium metabisulfite in the medical compound is below or equal to 0.05 mg/ml. It is desirable to use as little sodium metabisulfite as possible since it can affect the medical composition, provided that an acceptable and/or desired shelf life can be achieved. A reason is that the sodium metabisulfite breaks down adrenaline. Sulfites can cause allergy like reactions (intolerances); most commonly asthma symptoms in those with underlying asthma, sometimes allergic rhinitis (hay fever) like reactions, occasionally urticaria (hives) and very rarely, anaphylaxis (severe allergic reactions). Wheezing is the most common reaction. Oxygen scavenger concentration can be reduced/minimized by preventing oxygen ingress. This can be advantageous if the scavenger also contributes to chemical degradation of the active ingredient, which is true for e.g. adrenaline in combination with e.g. sodium metabisulfite, or if authorities demand a reduction of preservative amounts. The auto injector 1 and method for packaging it disclosed in this document minimizes, and may even remove the need for, the use of oxygen scavengers as will be further explained below.

The auto injector 1 comprises a hollow auto injector body 2 defining a space housing the medicament container. The shape of the auto injector body 2 can be adapted to house different kinds of medicament containers. The auto injector body 2 is, according to some aspects, also adapted to house other parts of the auto injector 1, such as a spring, if there is a spring-loaded syringe. Another example is that the auto injector body 2 may house a pressurized gas container if the auto injector 1 is a gas jet auto injector which uses pressurized gas to propel a fine jet of the drug through the skin of the patient without using a needle.

The auto injector body 2 is elongated having an elongated part, a first end side 21 and a second end side 22 opposite the first end side 21, as illustrated in the figures, and at least one through hole 3 arranged through the auto injector body 2 between the first and second end sides 21, 22. The at least one through hole 3 allow for flow of gas through the auto injector body 2 when the auto injector body 2 houses the medicament container. Another word for through hole is gas channel since the through holes are passages for allowing gas to flow through the auto injector body from one end side to the other. In other words, the at least one through hole is an uninterrupted passage for allowing gas to glow through the auto injector from one end side to the other. The through holes, i.e. the gas channels, are holes going through the auto injector body, from one end side to the other, also when the medicament container is in place in the auto injector body. It should be noted that the at least one through hole does not need to be a straight hole through the auto injector, it only needs to be a through hole, or in other words gas channel, between the end sides. Different designs of the at least one through hole 3 are illustrated in the figures. By designing an auto injector 1 with through holes where gas can flow through it, it is possible to package it such that the air inside the auto injector 1 is removed in a simple, fast and reliable manner. In the method for packaging described below, air may be removed from the package and inert gas may replace it. The at least one through hole 3 will help in emptying the package from air by allowing the air, and the protective gas that is to replace the air, to flow through the auto injector 1; otherwise there is a risk that there will form air pockets in the auto injector 1. In other words, the through holes make sure that there are no air pockets inside of the auto injector 1 such that the amount of air removed from the package is maximized. The design thus allows for minimizing the presence of atmospheric gases in the package with the auto injector 1.

Figure 6:
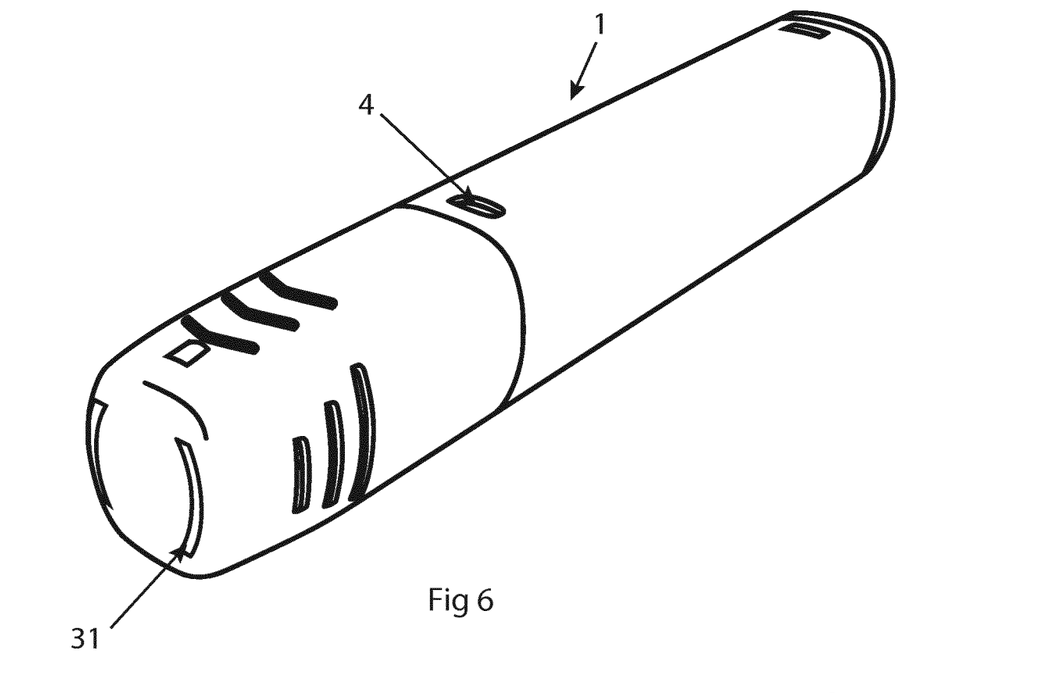
FIG. 6 shows an example of an auto injector with through holes with elongated shape
Figure 7:
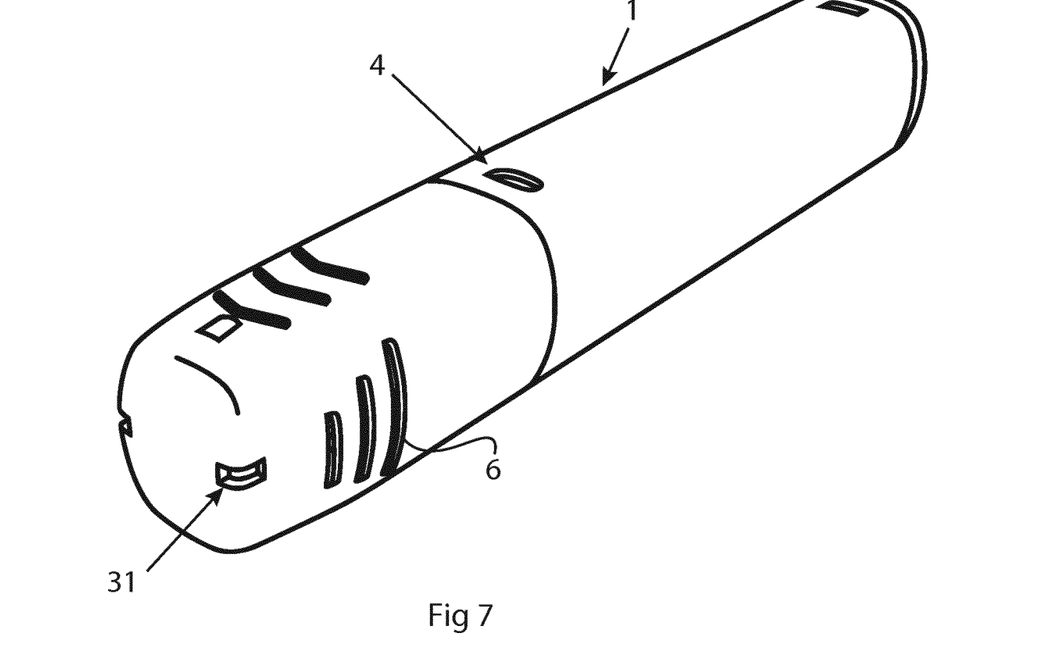
FIG. 7 shows an example of an auto injector with through holes which goes over the edge of the end side

According to some aspects, the at least one through hole 3 each comprises two through hole openings 31. In other words, each through hole has an opening in each end of the auto injector. It should be noted that if there are more than one through hole, they may share the same opening through the auto injector but have different openings in the end sides. Such an example is illustrated in FIG. 3 which shows two through holes with a total of four through hole openings, but the gas will flow in the same space inside of the auto injector. There are many aspects that will influence the choice of size, shape and numbers of the through hole openings 31. One aspect is simply aesthetics. Another aspect is which gases are to flow through the through holes. Different gases have different fluid dynamics and will flow differently in the same through hole 3. Therefore, the size of the diameter of the through hole opening 31 may depend on the inert gas chosen in the below described method. According to some aspects, the through hole openings 31 have a diameter equal to or larger than 0.5 mm. There may be diameters that are less than 0.5 mm depending on the shape of the through hole opening 31 and the number of through holes. If only one through hole 3 is used, the through hole opening 31 has, according to some aspects, a diameter equal to or larger than 0.1 mm. The shape of the through hole opening may also depend on the fluid dynamics of the gases used and also aesthetics. Examples of shapes of the through hole openings are illustrated in FIGS. 6 and 7. In FIG. 6, there are two through hole openings illustrated which have an elongated, curved shape and in FIG. 7, there are two openings that are elongated and arranged over the edge of the auto injector. The at least one through hole opening 3 is for example in a circular shape, in a rectangular shape, in an oval shape, in a square shape or in a triangle shape. The at least one through hole opening 31 may be in any shape that allows for the gases used to flow through. The two openings of the same through hole may be the same shape or different shapes. According to some aspects, the at least one through hole 3 comprises at least two through holes with through hole openings symmetrically arranged on the first and second end sides 21, 22. If several through holes are used, the openings may be arranged symmetrically on the end sides such that it is aesthetically pleasing. The symmetry may also be beneficial in preventing air pockets because it ensures a maximum coverage of the end sides with through holes. When there are more than one through holes, the shape of the through holes is not necessarily the same.

The size of a through hole 3 will determine the flow rate of gas through it. The hole should be large enough to allow for gas to flow fast enough to be useful when packaging the auto injector 1. The size needed for the at least one through hole 3 will depend on what gases are used, what kind of technique is used for removing the air and filling with inert gas, the number of through holes and the shape of the through hole; the shape may have a big influence on how the gas flows.

It should be noted that there are numerous different designs of auto injectors which houses different kinds of medicament containers. For the purpose of the disclosure, the design is irrelevant as long as there is at least one through hole, i.e. gas channel, going through the length of the auto injector body such that gas can pass through it when the medicament container is housed in the auto injector body. The disclosure is thus applicable to all types of auto injectors with prefilled medicament containers.

An example of a design of an auto injector is as follows: 6 through holes are positioned in a circular shape, symmetrically on both endings of the auto injector at approximate half distance between the middle of the short side and the outer edge. Hole diameter is approximately 1-1.2 mm for the openings. The holes are positioned in a manner that allows air to pass freely through each single opening into the inside of the auto injector. If there is something in the auto injector blocking an opening, then positioning may be varied according to following order: move the circle of openings further towards edge, group the openings in groups of two (a pair of holes) where each pair of openings is positioned symmetrically at one of the edges of the auto injector. No hole should be positioned so that it can be mistaken as opening for an emerging cannula.

The location of the at least one through hole 3 may also affect the flow of gas through them. According to some aspects, at least one through hole opening 31 is located partly on an end side 21,22 and partly on the elongated part of the auto injector 1 such that the opening 31 is located on the edge of the end side. In other words, the through hole 3 may be located over the edge of the auto injector 1 so that it is located on both an end side and on the elongated part. This is illustrated in FIG. 7 which shows two through hole openings located on the edge of the auto injector. The through hole 3 may be positioned like this on both end sides of the auto injector 1 or on one end side. A through hole 3 that goes over the edge of the end side and to the elongated part may prevent air pockets to form in the package on both the end sides and on the sides of the auto injector 1.

The medicament container is, according to some aspects, at least partly transparent and the auto injector body 2 is provided with at least two apertures 4 arranged on opposite sides of the medicament container allowing for visual control of the medical composition inside the container, wherein the apertures 4 form a visual line through the auto injector body 2 which is non parallel with the longitudinal axis of the auto injector body 2. Visual control of the medical composition, i.e. the drug inside the auto injector 1, is important so that the user can easily check if there is something wrong with the drug; for example, if the container is broken such that the drug is leaking out or that the drug has changed colour, for example due to oxygen exposure. Two, or more, control windows will allow for visual control with light from behind to improve the controllability of e.g. particles and/or discoloration. Since the drug may be exposed to light, possibly including UV light depending on the light absorption properties of the packaging of the auto injector 1, a light sensitive drug, such as adrenaline, can be affected negatively. This can be mitigated by covering the inspection apertures 4 in the auto injector 1 body with UV absorbing, transparent foil. However, this makes gas exchange in the auto injector body 2 even more difficult and the presence of ventilation openings, i.e. the at least one through hole 3, even more important.

Thus, according to some aspects, the at least one through hole 3 is connected with the at least two apertures 4 inside the auto injector 1 such that the gas can flow between the at least one through hole 3 and the apertures 4. This aspect allows for gas to flow from one end to the other but also from the sides to the ends. This may further prevent air pockets from forming in the packaging process.

The two apertures 4 are for example arranged as a through hole straight through the auto injector 1 so that there is a visual line straight through. According to some aspects, the at least two apertures 4 are arranged as a through hole through the auto injector body 2 which is perpendicular to the at least one through hole 3 arranged between the first end side 21 and the second end side 22. This is an example of how the holes are arranged with respect to each other. The through holes may also be tilted in respect of each other; it is a question of implementation and which angles gives the best gas flow and still allows for visual control of the drug.

Figure 8:
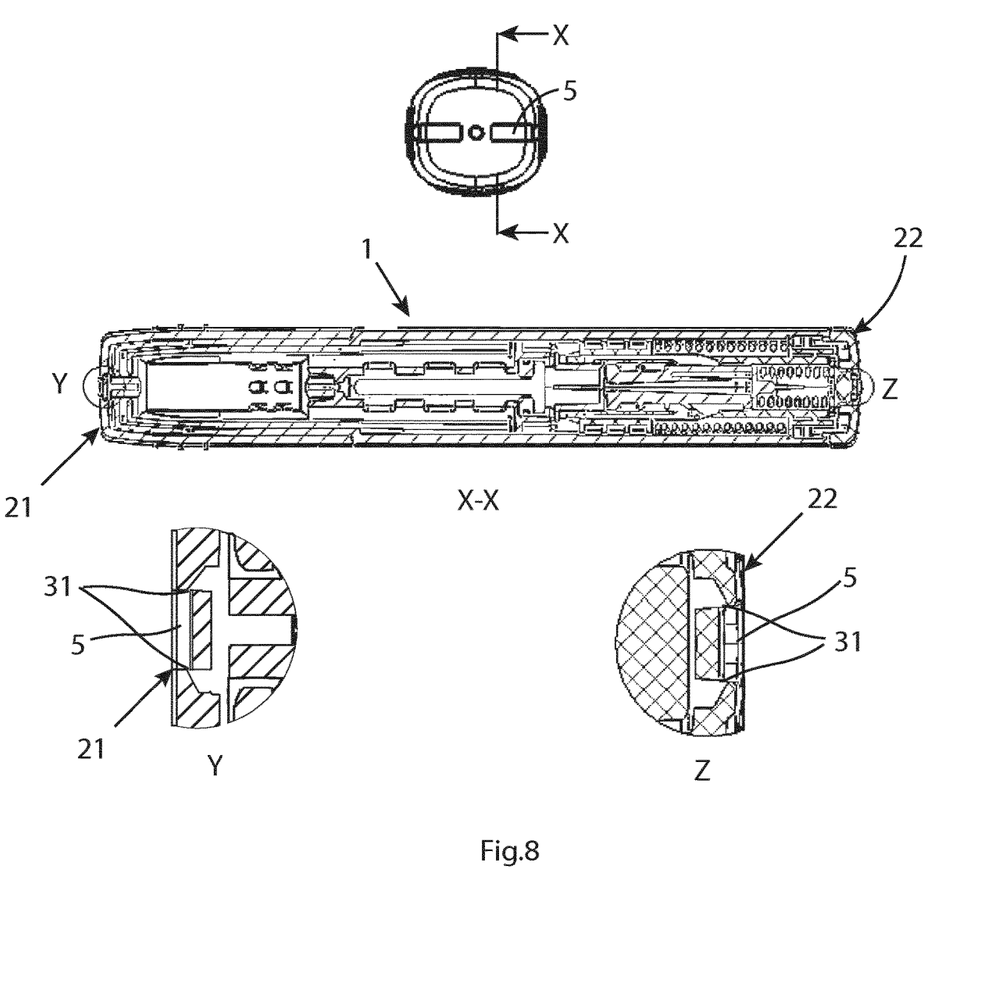
FIG. 8 shows an example of a cut through of an auto injector with enlarged parts

FIG. 8 shows a cut through of an example auto injector with through hole openings 31 in recesses 5 at the end sides. The top figure shows where in the auto injector the cut through is made, at X. Y and Z are enlarged parts of the middle of the end sides for an enlarged view of the through hole openings.

The through hole openings 31, i.e. holes or slits, are positioned in such way that ventilating gas that enters through the holes can continue through the body 2 of the auto injector and leave the auto injector on the opposite side of the auto injector. According to some aspects, the at least one of the end sides 21, 22 comprises a recess 5 and each through hole opening 31 on that side 21, 22 is arranged at a wall of said recess 5 so that each through hole opening 31 is arranged perpendicular to the end side 21, 22. The through hole openings 31 are thus designed in such way that the end user will not assume that the hole could be the place where the needle will emerge from the penetrating device. This is because the end user may be confused about which side is to be put against his/her body when using the auto injector 1 is both sides have holes where it can be expected that a needle will come out upon usage. The through hole openings can therefore be designed such that they are less noticeable and that there is no direct line to the inside of the auto injector. By doing so, confusion of the end user with respect to the purpose of such openings can be minimized. Further, ingress of dirt/dust is more difficult.

The recess 5 can be several recesses 5, such as one recess 5 per through hole opening. The recess 5 is for example an indentation or depression in the end side. The recess 5 has a bottom which surface is parallel with the surface of the end side and a wall which is substantially perpendicular to the surface of the end side and the bottom. The wall of the recess may also have an inclination compared to the surface of the end side and the bottom of 75-90°, wherein 90° is perpendicular to the surface and bottom.

Figure 9:
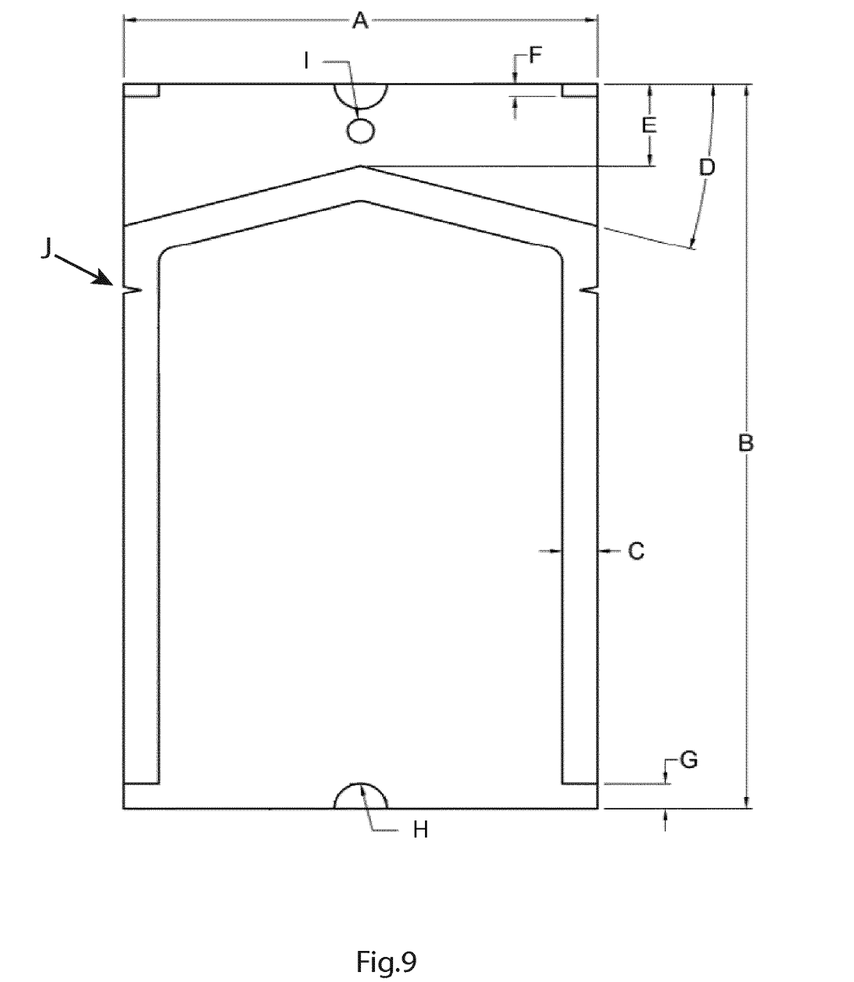
FIG. 9 shows an example of air flowing through an auto injector at the end sides and in a cut through FIG. 10 shows an example package for the auto injector

FIG. 9 shows an example auto injector with arrows indicating how air or gas is flowing through it. In this example, the end sides have recesses 5 where the through hole openings 31 are located in the walls of the recesses. The top two figures are the end sides 21,22 and the bottom part shows a cut through of the example auto injector. In the middle of the cut through of the auto injector, the medicament container is visible and to its left a needle for administering the content of the medicament container to the end user is visible. In this example, the through hole openings 31 are in the shape of slits in the wall of the recesses 5.

The medical composition comprises, for example, adrenaline. Adrenaline is sensitive to oxygen and it would be beneficial to use in the auto injector 1 according to the disclosure for reasons explained above.

An advantage with an auto injector which has through holes between the end sides is that the package can be made much more narrow than conventional packages. This is because air behind the auto injector will be evacuated through the through holes and not via the sides of the auto injector. This reduces the amount of packaging needed and it also makes the packaged auto injector easier to handle for the end user. The package for an auto injector according to any of the above is disclosed, wherein the package is a pouch and the inside of the pouch is at least 70 mm longer than the length of the auto injector and has a maximum width, at the most narrow part of the pouch, of 30 mm wider than the width of the auto injector. According to some aspects, the inside of the pouch is at least 80 or 90 mm longer than the total length of the auto injector.

Figure 10A:
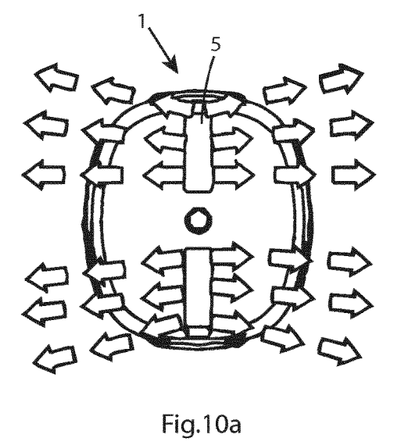
Figure 10B:
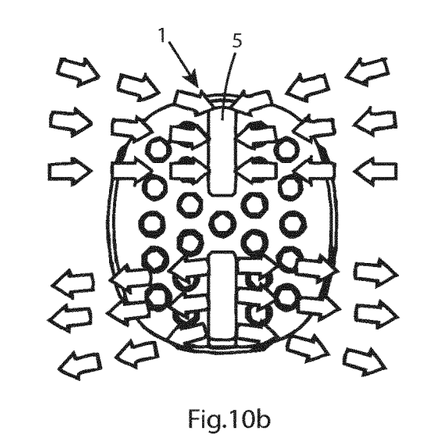
Figure 10C:
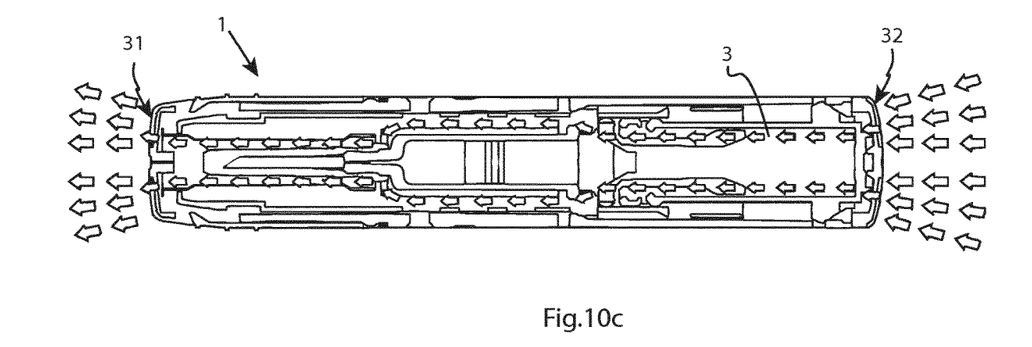

An example package is shown in FIG. 10. The illustration is merely an example and the measurements are to be adapted depending on the size of the auto injector and on which type of method is used for removing air from the package. The example of FIG. 10 is a pouch which has a width A of 95 mm and a length B of 307 mm. This example pouch is for an auto injector with the dimensions 150±1 mm in length and between 23.4 and 27.4±0.5 mm in width. The seal width C is 10 mm and it is a seal between two sides of the pouch. The chevron angle D is 15° and the distance E between the chevron tip and the cut off is 20 mm. The pouch has a tack seal F of 6 mm at the cut off and may have an end gap G at the opposite side. A thumb notch H may be provided for opening the package for retrieving the auto injector. A hang hole I may be provided for hanging the packaged auto injector. The hang hole I is preferably centred and may be 3 mm from the sealed end. In this example, tear notches J are provided on both sides of the package do reduce risk of failure of opening the package to retrieve the auto injector in an emergency. The tear notches J may have a depth of about 1.6 to 2 mm. Peel strength of the illustrated example may be for example around 0.18 kg/cm$^2$.

According to an embodiment of the disclosure, it comprises a packaged auto injector set comprising the pouch according to above with the inside of the pouch being at least 70 mm longer than the length of the auto injector and the maximum width, at the most narrow part of the pouch, being 30 mm wider than the width of the auto injector. The packaged auto injector set comprises that the package is filled with the auto injector according to any of the above, wherein the package filled with the auto injector is snugly arranged in a neoprene sleeve such that the movement of the auto injector relative the package is prevented. Since the package can be made narrow due to the through holes, there will not be a lot of packaging material around the auto injector. It is therefore easy to store this packaged auto injector set in a neoprene sleeve; there is not a lot of package that needs to be held in when putting it in the sleeve. The neoprene sleeve protects the packaged auto injector from physical damage, keeps the temperature of the auto injector more constant and minimizes movement of the packaged auto injector and thus minimizes friction which can lead to punctures. The neoprene material is in latex form.

Figure 11:
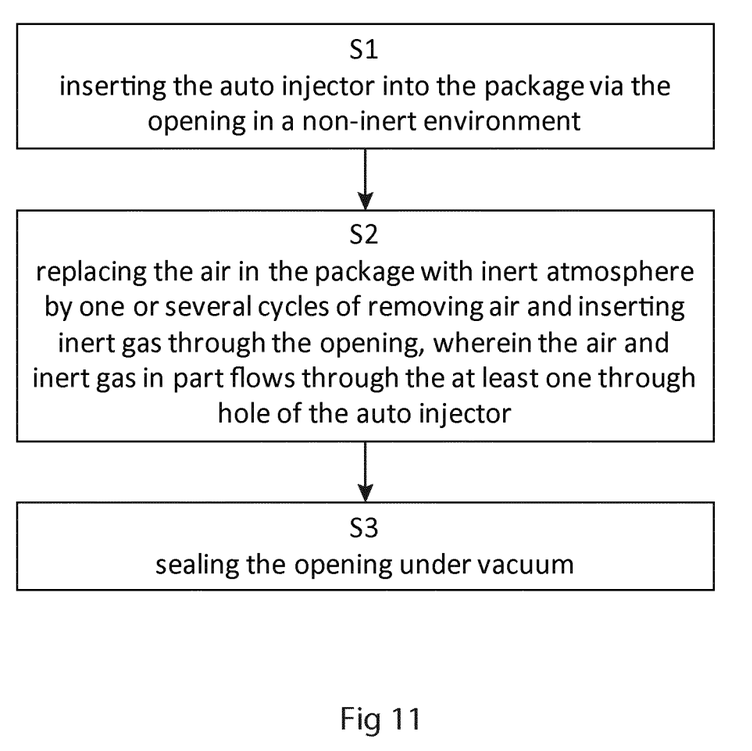
FIG. 11 shows a block diagram of the method

FIG. 11 shows a block diagram of the method. The method comprises a method for filling a package with an auto injector 1 according to any one of the above aspects. The package comprises an opening. The size of the opening will depend on the type of equipment used for the packaging of the auto injector 1. The package is for example a square shaped or rectangular pouch and the opening is according to some aspects located on one of the sides. The method comprises inserting the auto injector 1 into the package via the opening in a non-inert environment. The auto injector 1 is preferably inserted such that the at least one through hole is directed towards the opening. According to some aspects, at least one opening of the at least one through hole 3 is directed at the opening.

The method further comprises, in a non-inert environment and under atmospheric pressure:

replacing the air in the package with inert atmosphere by one or several cycles of removing air and inserting inert gas through the opening, wherein the air and inert gas in part flows through the at least one through hole 3 of the auto injector 1. The method further comprises sealing the opening under vacuum. As previously discussed, the through holes allow for the auto injector 1 to be packaged in a non-inert environment according to above because they allow for oxygen to leave the package efficiently through the holes and fills the whole package, including the through holes inside the auto injector 1 with inert gas. The achieved efficiency in removing air and inserting inert gas in the package and partly through the at least one through hole 3 makes it possible to perform these steps under atmospheric pressure. That is, the packaging does not need to be performed under hard vacuum. Some negative pressure is advantageous but the amount of negative pressure can be limited by possible plunger movement of syringes containing a gas bubble. To perform the packaging under hard vacuum will lead to plunger movement which may compromise the sterility.

Figure 14:
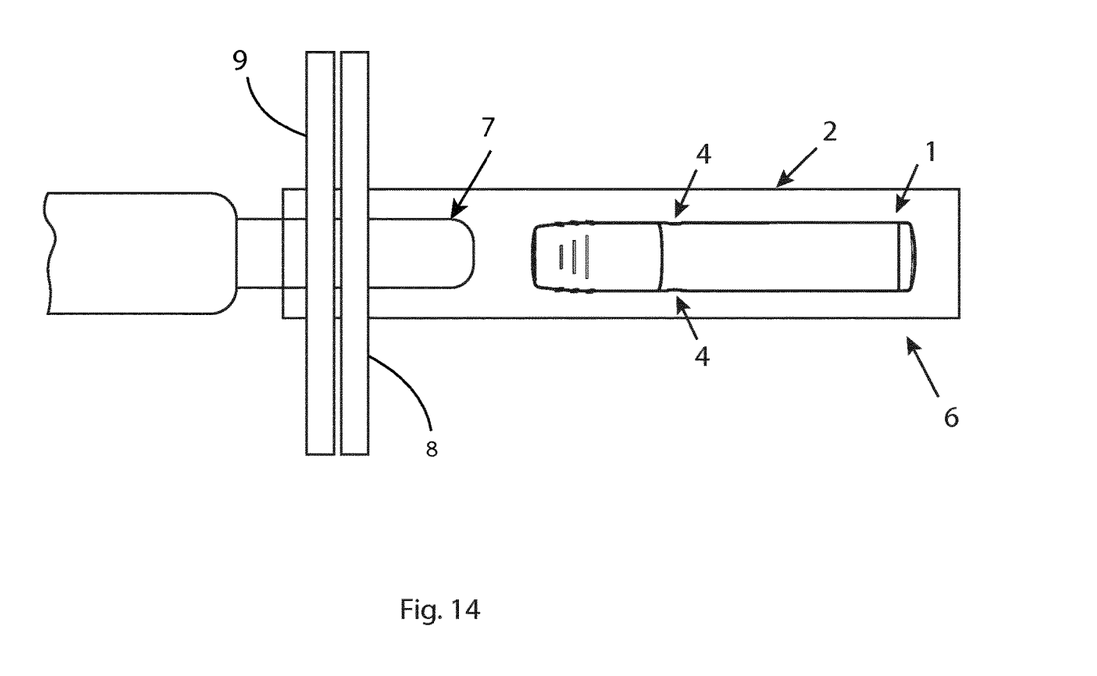
FIG. 14 shows an example of a nozzle type vacuum sealing machine

The air is, according to some aspects, removed using a nozzle type vacuum sealing machine. An example of such a machine is illustrated in FIG. 14. It has a nozzle 7 that is inserted in the opening of the package and removes the air through the nozzle. This type of machine provides a local point in the opening for removing the air which is an effective way of only removing the air that is in the package. A nozzle type vacuum machine is known in the art and has a nozzle for removing air and inserting gas through an opening in the package. The machine has a welding bar 8 that is pressed down on the package to seal it at the end of the packaging process. The welding bar seals the package preferably by heat. The machine also has a seal lip 9, preferably made of rubber, that pushes down on the package on and around the nozzle to keep it sealed when the nozzle is removing air and inserting gas. The seal lip is also pushing down on the package while withdrawing the nozzle to prevent air leakage during the withdrawal. In other words, the seal lip keeps the package closed during removing air and inserting gas and when the process is completed, the welding bar seals the package.

Another aspect why ventilation openings, i.e. the at least one through hole 3, at the auto injector 1 ends is advantageous for such a pouching process: during sucking cycle, air is first removed from pouch inside-surrounded by pouch, since pouch walls are flexible. Air always takes the easiest path. As a consequence, the pouch walls will get attached to the sides of the auto injector body 2. Possible ventilation openings on auto injector body 2 sides, i.e. the long sides, get obstructed by the pouch walls. The best path for air to be removed from inside the auto injector 1 is via ventilation openings at the end sides, where the nozzle points at.

The length of the previously discussed package will be affected by the type of machine used to remove the air. In a nozzle type vacuum machine, the distance between the nozzle and the auto injector affects the efficiency of air removal. A distance between 15-30 mm, and preferably between 20-25 mm is efficient when removing air. A shorter distance may lead to problems when sealing the package such that it is not vacuum sealed. A longer distance may lead to inefficient air removal.

When the auto injector, i.e. AI, is inside the pouch and is to be purged with inert gas, e.g. N2, and vacuum-pouched with a nozzle type vacuum sealer/welder, there are two major challenges:

1) When the AI (inside the pouch) is placed too close to the end of the nozzle then, the pouch opening is forced open, by the height of the AI, in an example case 24.4 mm, in proximity of the sealing/welding bar. Thus, no robust sealing process is possible, because the risk for wrinkles, due to the forced widening of the pouch opening, is too great.

2) When the AI inside the pouch is placed too far away from the nozzle ending, then the pouch prevents proper emptying of the pouch through the nozzle, since the pouch is closed between the AI and the nozzle during the sucking cycle. This is negative, since the necessary negative pressure (for pouch integrity control by the user) cannot be achieved and the purging of O2 and replacement with N2 becomes inefficient.

For an AI of the dimensions of 150±1 mm in length and 23.4±0.5 mm in width, it has been discovered that an optimal distance of AI and nozzle lies between 20 and 25 mm. Acceptable results might be achievable also for a wider range, 15-30 mm.

For an AI of greater width, e.g. 40 mm, a greater distance between AI and nozzle can be maintained, e.g. 30-40 mm. This ascertains that the pouch can be sealed/welded with acceptable risk for seam wrinkles; also the pouch is opened wider preventing that the nozzle opening is "sealed" during the sucking cycle.

For an AI of lesser width, e.g. 18 mm, a shorter distance between AI and nozzle can be maintained, e.g. 15-20 mm. This ascertains that the pouch can be sealed/welded with acceptable risk for seam wrinkles; there is enough distance between sealing bar and pouch-spreading device; also the pouch is opened less, therefore a shorter distance is sufficient to prevent that the nozzle opening is "sealed" during the sucking cycle.

Further, the following parameters are relevant:

The distance between the AI and the outer edge of the sealing/welding bar: This may be at least 5-6 cm distance from the AI inside the pouch. This parameter is connected to the seal-wrinkle issue. If the sealing bar is too close to the AI of a width of 24.4 mm, then seal wrinkles, and thus leakage, is a major risk and no robust sealing process is possible. Longer distances between the sealing/welding bar and the AI can be acceptable, but then the nozzle length should be adjusted to control the distance between the nozzle opening and the AI.

The vacuum purging and sealing process works more reliably if the seal lip, where a seal lip is of rubber like material and pushes the two sides of the pouch together, during suck/blow cycles and also when the nozzle is pulled out of the pouch right before welding, is positioned on the opposite side, relative to the AI, of the sealing bar to avoid sealing wrinkles. Also, the pouch may leak during the vacuum cycles if the lip is on the AI side and thus too close to the widening effect of the AI. Consequently the pouch is, according to some aspects, long enough to fit the AI, to allow enough distance between AI and nozzle opening as previously described, to allow enough distance between AI and sealing bar and to allow that the open, unsealed side of the pouch, on the "other" side of the sealing/welding bar relative to the AI, stretches far enough to be completely covered by the sealing seal lip.

Exact dimensions of the pouch depend on the dimensions of the sealing/welding bar and the seal lip.

Figure 12:
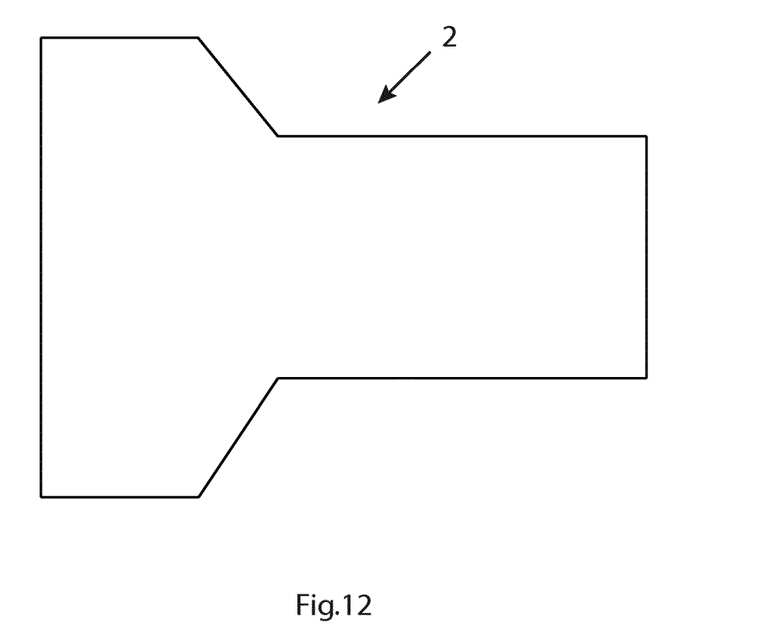
FIG. 12 shows an example shape of a package for the auto injector
Figure 13:
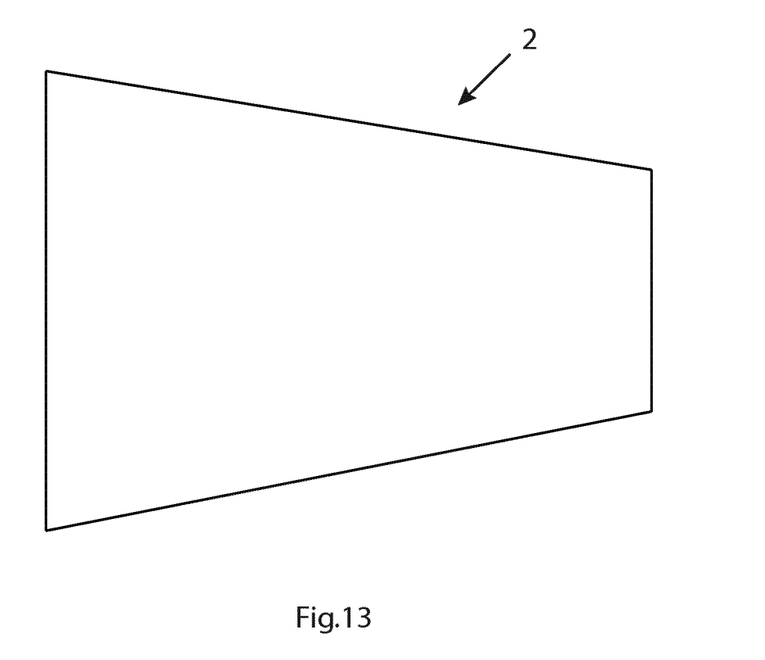
FIG. 13 shows an example shape of a package for the auto injector

Pouch dimensions: The width of the open side of the pouch, that is being sealed/welded at the end of the vacuum pouching process, may have a minimum width of 80-100 mm. The pouch can have this width over its complete length. However, if pouch material is to be minimized then a pouch can be used that has an unsealed opening of 80-100 mm and that narrows to the AIs width, for example ca 30-40 mm, in sufficient distance to the sealing/welding bar. This may also have the advantage that the AI is fixated in a certain position and can ideally not move inside the pouch during the purging cycles. Two examples of how the pouch may be shaped are shown in FIGS. 12 and 13. In FIG. 12, the opening is two the left and there is a tapering section for reducing the width of the pouch. In FIG. 13, the whole pouch is tapered, from the opening to the left to the other end. As previously discussed, the dimensions of the pouch are, according to some aspects, that the inside of the pouch being at least 70 mm longer than the length of the auto injector and the maximum width, at the most narrow part of the pouch, being 30 mm wider than the width of the auto injector. This means that in the illustrated examples of FIGS. 12 and 13, the right part of the pouch has a maximum width on the inside of 30 mm wider than the auto injector to be placed in the pouch.

An example of the packaging process will now be described with example devices.

Step 1: Pouching; consisting of inserting the auto injector 1 into the pouch, which is sealed on three sides Step 2: Replacing air in the pouch with inert atmosphere, e.g. nitrogen, in one or several cycles of sucking air and blowing e.g. nitrogen Step 3: Vacuum sealing.

The pouching achieves:

Removal of "enough" oxygen from the inside of the pouch and the auto injector 1 and replacing it with inert gas. The more oxygen is removed during this process, the longer shelf life can be achieved. Data that shows that 36 M of shelf life can be achieved when reaching <=1% oxygen in the pouch. This also allows for storage of an auto injector comprising adrenaline for longer than one year at 40° C.

Sealing of the pouch in a vaccumized look; it should be clearly visible that hardly any gas is in the pouch except for the inert gas that is inside the body of the auto injector 1; i.e. no bubbles in the package. It also allows the patient to check pouch integrity. If the pouch loses the vaccumized look, a hole can be assumed and the product has to be replaced. This procedure allows easy packaging integrity control without e.g. $O_2$ sensor inside the pouch (which would be an alternative approach but which makes packaging much harder since packaging has to be performed under inert gas to avoid a triggering of $O_2$ chemical sensor).

For primary containers that contain a gas bubble: avoiding of an excess of negative pressure:
 during pouching—to avoid plunger movement which may affect sterility of the drug Vacuum chamber pouching is unsuitable to achieve the above listed requirements. It requires too low negative pressure during pouching for an acceptable vacuumed look of the pouch, which might lead to plunger movement. A desired pouching process removes air from the pouch while the pouch is subjected to atmospheric pressure; which is disclosed in the method discussed above.

An example of the process of providing a packaged auto injector will now be described in more detail.

1) Pre-fillable syringes are filled with drug product. Syringe is not a gas tight system (gas tight plungers are not available and the needle shield is by design permeable for gas- to allow sterilization by ethyleneoxide 2) Filled syringes are stored 10-12 weeks 3) After release, ca 12 weeks after filling, syringes will be assembled into auto injectors, the auto injectors are labelled and vacuum pouched:
 a. Pouches, i.e. packages, have been optimized in dimensions. Pouches may have transparent part to allow visual control of drug
   i. Pouches are only slightly wider than the Auto injectors to minimize bulkiness of pouched auto injector
   ii. Pouches being so narrow requires ventilation through the auto injector (1 to change atmosphere inside auto injector and 2 to allow gas flow from the opposite end of the narrow pouch)
   iii. Pouches is significantly longer than device (ca 70 mm or more) because narrow pouches are forced open by auto injector body; this may make the welding of the open side of the pouch unreliable (wrinkles lead to leaks of closing weld seam)
 b. Pouches are atmosphere exchanged by nozzle type vacuum welding machine. Only nozzle type allows the two following requirements
   i. Vacuum during and after pouching process is never <500 mbar (otherwise plunger movement could lead to loss of sterility)
   ii. Vacuum after pouching is between 500 mbar and ca 750 mbar (TBC) to allow vacuumed feel and look of pouch (regulatory requirement to be able to control pouch integrity for end user)
 c. After completed pouching, the pouched auto injectors are packed in carton together with neoprene sleeve as accessory Neoprene sleeve is to protect pouch during transport and throughout shelf life (3 years). The neoprene sleeve sits tight around pouched auto injector which minimizes movement and thus friction and thus risk for puncture. It also dampens fall and temperature changes during end user transport.

REFERENCE LIST

1. Auto injector
2. Auto injector body
21. First end side
22. Second end side
3. At least one through hole
31. At least one through hole opening
4. At least two apertures
5. Recess
6. Grip 7. Nozzle
8. Welding bar
9. Seal lip

The invention claimed is:

1. An auto injector for administrating a medical composition, the auto injector comprising:
a prefilled liquid medicament container comprising the medical composition,
a hollow auto injector body defining a space housing the medicament container, wherein the auto injector body is elongated having an elongated part, a first end side and a second end side opposite the first end side, and
at least one through hole arranged through the auto injector body between the first and second end sides, whereby the at least one through hole allow for flow of gas through the auto injector body when the auto injector body houses the medicament container, and
wherein the medicament container is at least partly transparent and the auto injector body is provided with at least two apertures arranged on opposite sides of the medicament container allowing for visual control of the medical composition inside the container, wherein the apertures form a visual line through the auto injector body which is non-parallel with the longitudinal axis of the auto injector body, and
wherein the at least one through hole is connected with the at least two apertures inside the auto injector such that the gas can flow between the at least one through hole and the apertures.

2. The auto injector according to claim 1, wherein the at least one through hole each comprises two through hole openings.

3. The auto injector according to claim 2, wherein the through hole openings have a diameter equal to or larger than 0.5 mm.

4. The auto injector according to claim 2, wherein at least one through hole opening is located partly on an end side and partly on the elongated part of the auto injector such that the opening is located on the edge of the end side.

5. The auto injector according to claim 2, wherein the at least one through hole comprises at least two through holes with through hole openings symmetrically arranged on the first and second end sides.

6. The auto injector according to claim 2, wherein the at least one of the end sides comprises a recess and each through hole opening on that side is arranged at a wall of said recess so that each through hole opening is arranged perpendicular to the end side.

7. The auto injector according to claim 1, wherein the medical composition comprises adrenaline.

8. The auto injector according to claim 1, wherein the medical composition comprises a chemical oxygen scavenger.

9. A package for an auto injector according to claim 1, wherein the package is a pouch and the inside of the pouch is at least 70 mm longer than the length of the auto injector and has a maximum width, at the most narrow part of the pouch, of 30 mm wider than the width of the auto injector.

10. A packaged auto injector set comprising a package for an auto injector, wherein the package is a pouch and the inside of the pouch is at least 70 mm longer than the length of the auto injector and has a maximum width, at the most narrow part of the pouch, of 30 mm wider than the width of the auto injector, and wherein the package is filled with the auto injector according to claim 1, and wherein the package filled with the auto injector is snugly arranged in a neoprene sleeve such that the movement of the auto injector relative the package is prevented.

11. A method for filling a package with an auto injector according to claim 1, the package comprising an opening, wherein the method comprises:
inserting the auto injector into the package via the opening in a non-inert environment, and
in a non-inert environment and under atmospheric pressure:
replacing the air in the package with inert atmosphere by one or several cycles of removing air and inserting inert gas through the opening, wherein the air and inert gas in part flows through the at least one through hole of the auto injector,
and
sealing the opening under vacuum.

12. The method according to claim 11, wherein the air is removed using a nozzle type vacuum sealing machine.

13. An auto injector for administrating a medical composition, the auto injector comprising:
a prefilled liquid medicament container comprising the medical composition,
a hollow auto injector body defining a space housing the medicament container, wherein the auto injector body is elongated having an elongated part, a first end side and a second end side opposite the first end side, and
at least one through hole arranged through the auto injector body between the first and second end sides, whereby the at least one through hole allow for flow of gas through the auto injector body when the auto injector body houses the medicament container, and
wherein the medicament container is at least partly transparent and the auto injector body is provided with at least two apertures arranged on opposite sides of the medicament container allowing for visual control of the medical composition inside the container, wherein the apertures form a visual line through the auto injector body which is non-parallel with the longitudinal axis of the auto injector body, and
wherein the at least two apertures are arranged as a through hole through the auto injector body which is perpendicular to the at least one through hole arranged between the first end side and the second end side.

* * * * *